United States Patent [19]

Advani et al.

[11] Patent Number: 4,462,246

[45] Date of Patent: Jul. 31, 1984

[54] PERCENT OXYGEN GAUGE

[75] Inventors: Gulu N. Advani, San Jose; Scott A. Amundson, Mountain View; Eli M. Goldfarb, Los Altos, all of Calif.

[73] Assignee: Sierra Monitor Corporation, Sunnyvale, Calif.

[21] Appl. No.: 385,188

[22] Filed: Jun. 4, 1982

[51] Int. Cl.³ ............................................ G01N 27/54
[52] U.S. Cl. ...................................... 73/23; 204/408; 340/632
[58] Field of Search ...................... 73/23, 19; 340/632, 340/633, 634; 204/406, 407, 408, 424, 431, 1 Y

[56] References Cited

U.S. PATENT DOCUMENTS

| | | |
|---|---|---|
| 3,266,293 | 8/1966 | Hubner ................................... 73/23 |
| 3,427,862 | 2/1969 | Hubner ................................... 73/23 |
| 3,562,521 | 2/1971 | Vanderschmidt et al. ............. 73/23 |
| 3,685,346 | 8/1972 | Molloy .................................... 73/23 |
| 4,189,725 | 2/1980 | Rowland ............................. 340/632 |
| 4,297,689 | 10/1981 | Shaw et al. ......................... 340/632 |
| 4,419,211 | 12/1983 | Brauer ................................. 204/408 |

Primary Examiner—Stephen A. Kreitman

[57] ABSTRACT

A gauge measuring percent oxygen by simultaneously measuring oxygen partial pressure and ambient atmospheric pressure with solid state transducers. Two electrical signals obtained from the transducers are combined in a summing amplifier in accord with an empirically determined relation to yield a percent oxygen value which is displayed. The gauge has provisions for using an internal oxygen partial pressure transducer or an external probe connected to the gauge by a cable.

10 Claims, 3 Drawing Figures

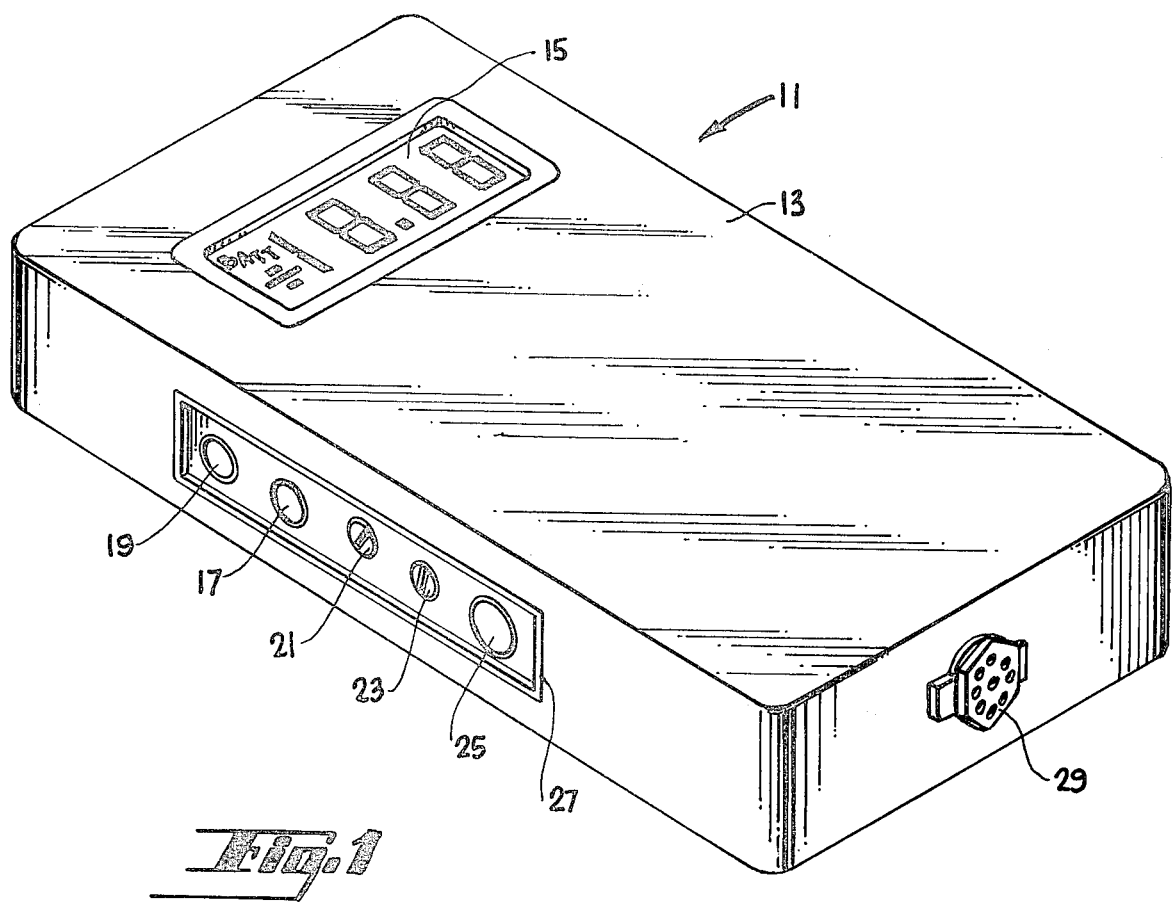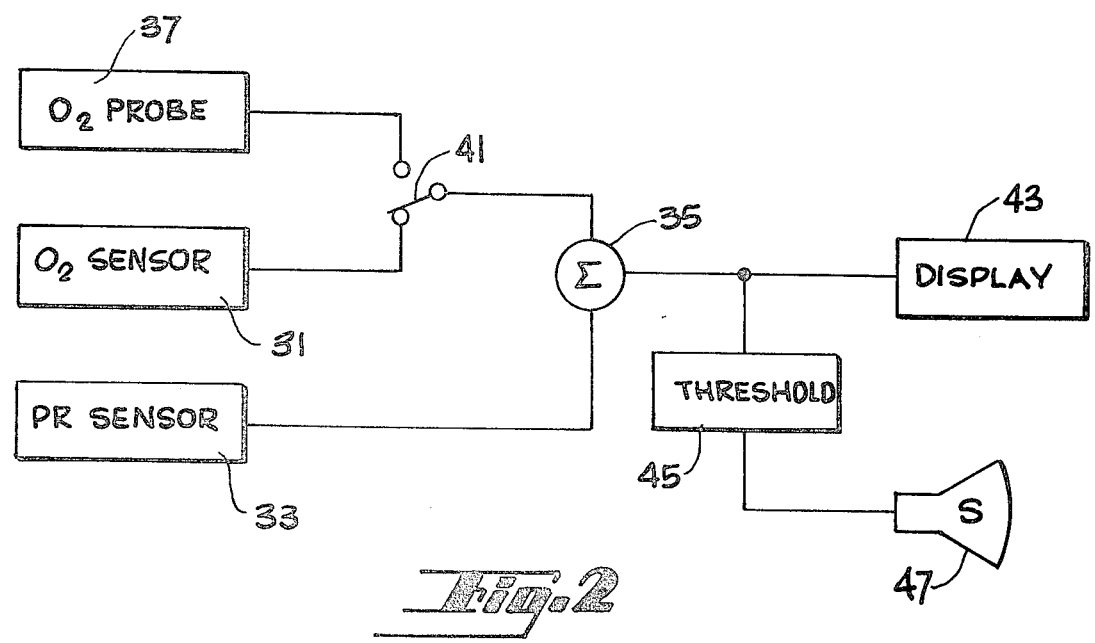

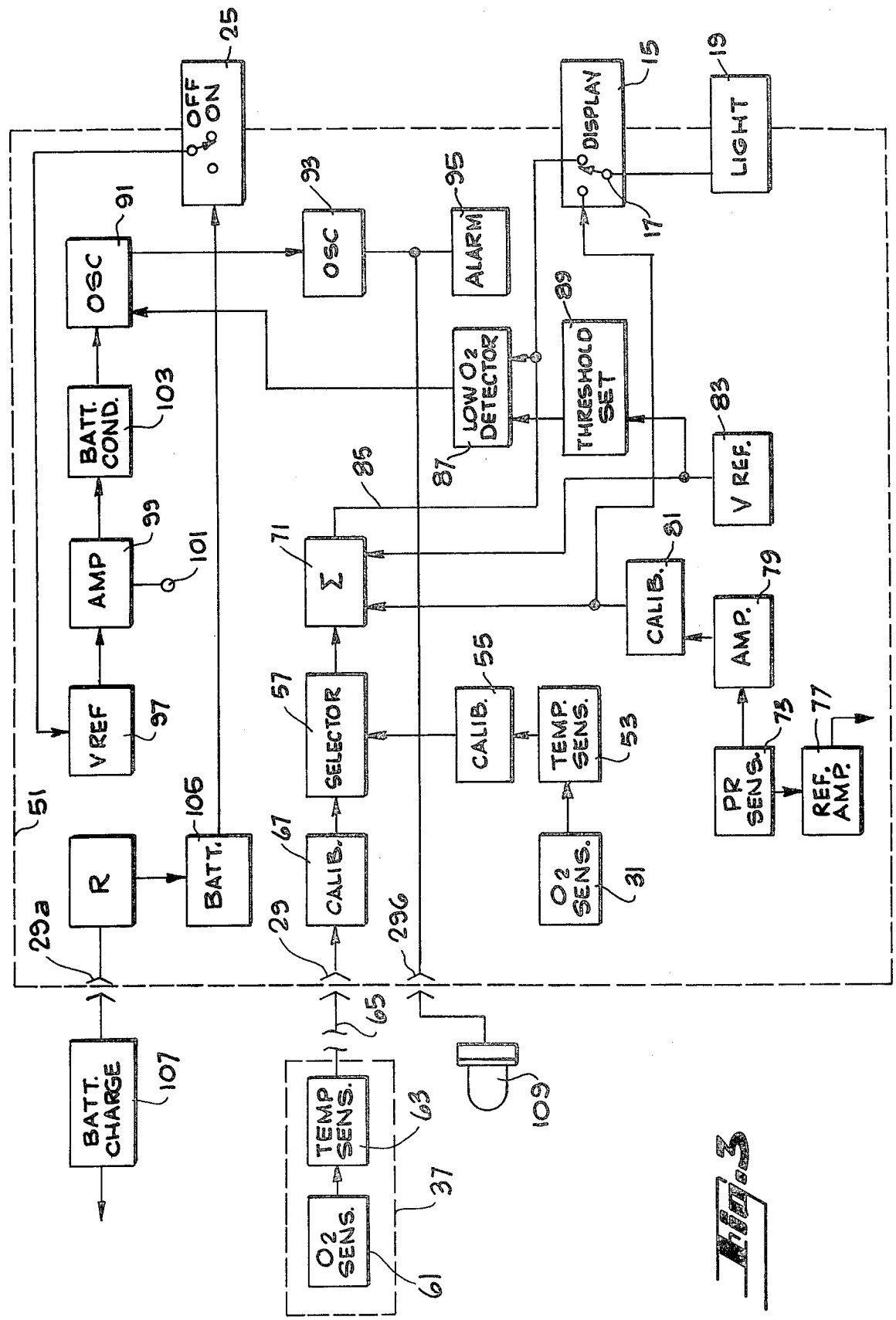

PERCENT OXYGEN GAUGE

DESCRIPTION

1. Technical Field

The invention relates to a gauge for measuring the percent oxygen in air, with automatic compensation for pressure variations.

2. Background Art

Electrochemical cells designed for the measurement of oxygen in ambient air have been used for several years. In such cells, oxygen is reduced at the sensing electrode, resulting in a current that is directly proportional to the concentration of oxygen.

Currently available instruments measure the partial pressure of oxygen and call this the percentage of oxygen in the atmosphere. The partial pressure measurement is correlated with the percentage of oxygen with a manual adjustment mostly commonly made without information about humidity, temperature, barometric pressure changes due to weather changes or barometric pressure changes due to elevation changes, for example in a mine shaft. Readings of percentage of oxygen will vary significantly for all of these conditions unless there is supplementary compensation, even though no change occurs in the percent oxygen on a ratiometric basis.

Under ideal conditions, the percentage of oxygen will be 20.9% Health and safety authorities specify that when the percentage falls to 19.5% or lower, this constitutes a hazardous environment. There are many conditions where reading the partial pressure and identifying it as the percentage oxygen can lead to life-threatening situations.

For barometric pressure changes due to changes in elevation or weather conditions, the readings given by prior gauges will usually show a change in the percentage of oxygen because they only measure oxygen partial pressure. In fact, the percentage of oxygen has not changed, as both the oxygen and nitrogen pressures will change together so that the ratio of the oxygen to nitrogen will be nearly constant. A drop in oxygen partial pressure due to dilutants could then be masked by barometric pressure changes with no differentiation because of reliance on manual correction procedures which have not been made.

An object of the invention was to devise a portable gauge for percent oxygen which automatically compensates for pressure variations.

DISCLOSURE OF INVENTION

The above object has been achieved with a gauge that samples ambient air and electrically combines signals representing oxygen partial pressure and atmospheric pressure to yield a percent oxygen reading. The electrical signals are derived from measurement transducers in a portable enclosure, equipped with an alarm for signalling low levels of percent oxygen. Humidity is treated as a contaminant and is not compensated, while temperature variations are corrected in the usual way. The gauge has a jack for an external oxygen sensing probe for remote use. When the probe is connected, the internal oxygen measurement transducer is disabled.

BRIEF DESCRIPTION OF DRAWINGS

FIG. 1 is a perspective view of a gauge in accord with the present invention.

FIG. 2 is a simplified block diagram of the gauge illustrated in FIG. 1.

FIG. 3 is a more detailed block diagram of the gauge illustrated in FIG. 1.

BEST MODE FOR CARRYING OUT THE INVENTION

With reference to FIG. 1 the gauge 11 is housed in a hand-held container 13 whose most prominent feature is a display 15. The display reads percent oxygen unless a switch 17 is depressed. In this case, the gauge will read atmospheric pressure. Another switch 19 provides backlighting for the display. Calibration screw 21 is for calibrating the internal oxygen sensor of the gauge. Screw 23 is for calibrating the external oxygen sensor. An on-off switch 25 applies power to the device, as well as switching off the power when the switch is depressed again. The screws 21 and 23, as well as push buttons 17, 19 and 25 are all slightly recessed, below the level of a finger guard 27 which presents accidental manipulation of the buttons or the screws. A jack 29 is provided for receiving an external oxygen probe as well as for use in receiving a battery charger or an ear phone with different connector pins. The dimensions of the container 13 are arbitrary, but preferably should be such that the unit can be held in one hand, like a calculator or portable dictating machine.

With reference to FIG. 2, a simplified diagram is presented showing the electrical construction of the percent oxygen gauge illustrated in FIG. 1. An internal oxygen sensor 31 and an internal pressure sensor 33 are connected to a summing junction 35. Alternatively, an external probe 37 when plugged into the jack 29, activates switch 41 such that the outputs of the probe 37 and pressure sensor 33 are summed in the summing junction 35. The output of summing junction 35 is an electrical signal for the panel meter type display 43. The same signal is transmitted to a threshold detector 45 for comparison against a preset level. When the signal from the summing junction 35 goes below the preset level an audible alarm is sounded in a speaker 47.

The output of the summing junction 35 is a linear combination of the pressure signal from pressure sensor 33 and an oxygen partial pressure signal from either internal oxygen sensor 31 or the external oxygen sensor in probe 37. The output signal from summing junction 35 is a pressure compensated oxygen signal which is read as a percent. The transfer function which is used to compute the percent oxygen in the summing junction is as follows:

$$\%O_2 = K_1(PO_2) + K_2(760 - P_{amb}) \tag{1}$$

where $K_1$ and $K_2$ are constants and $PO_2$ and $P_{amb}$ are the measured oxygen partial pressure and ambient atmospheric pressure, respectively. The constants $K_1$ and $K_2$ are selected by calibraion of the gauge. By careful selection of the constants, the gauge may be made accurate to within 5%, with a resolution of one-tenth of one percent for oxygen.

With reference to FIG. 3, a more detailed version of the circuits of the gauge may be seen.

The container housing the gauge is indicated by the dashed line 51. Projecting from the housing are the on-off push-button switch 25, the push-button switch 17 for selecting a display of atmospheric pressure, as opposed to percent oxygen and lastly, a push button 19 for illuminating the display 15. The gauge features an internal oxygen sensor 31 which is a standard partial pressure oxygen-measuring electrochemical cell. The output is an electrical signal which is fed to a temperature sensor 53 for providing temperature compensation in the usual way. For example, the sensor may be a thermistor which adjusts the oxygen signal for variations in temperature in accord with well-known relationships. The output of temperature sensor 53 is transmitted to a span calibration potentiometer 55 which adjusts the oxygen signal to be between a desired range of values. The output from this potentiometer is transmitted to a sensor selector 57 which selects between the internal oxygen sensor 31 and an external probe 37, depending upon whether the probe is plugged into the instrument or not. When the external probe 37 is plugged in to a jack 29, logic within the selector 57 causes the probe signal to replace the signal from the internal oxygen sensor 31. The probe 37 includes a partial pressure oxygen sensor 61 of the same type as oxygen sensor 31, together with a temperature sensor 63 similar to temperature sensor 53. Preferred oxygen sensors are Teledyne micro-fuel cells, class C-1. The probe is useful for measuring oxygen partial pressure in less accessible spaces, such as within wells, shafts, tanks and closed rooms. The output from probe 37 is taken along cable 65. This signal is a temperature compensated oxygen partial pressure signal. A potentiometer 67 provides span calibration, so that the signal arriving from cable 65 will have a desired range. The selected oxygen signal derived from selector 57 enters summing junction 71 for combination with an ambient pressure signal.

The pressure signal is derived from a temperature compensated atmospheric pressure transducer 73, typically a solid state device which may be purchased commercially. A preferred transducer is Honeywell PC 136A1L. Atmospheric pressure transducer 73 measures ambient pressure and produces a corresponding electrical signal. Pressure sensor 73 is grounded by means of a floating ground reference amplifier 77 which provides ground for all active devices within housing 51. The pressure measurement signal is transmitted to an amplifier 79 and then to a calibration potentiometer 81 which serves to set the span or range of the signal, similar to calibration potentiometer 67. The compensated and calibrated pressure signal is transmitted to the summing node 71. Summing node 71 combines the selected, temperature-compensated, oxygen partial pressure signal with the temperature-compensated pressure signal in accord with the transfer function given by equation (1). The summing junction 71 may be an operational amplifier which is biased by a reference supply 83 and having an output signal along wire 85, representing a computed percent oxygen value. This value may be displayed in display 15. The value is also transmitted to a threshold detector 87 which compares the percent oxygen signal to a preset threshold value established by a potentiometer 89 which provides the voltage drop from the reference supply 83. When this voltage level is exceeded by the percent oxygen signal received along line 85, the threshold detector 87 transmits a signal to oscillator 91 which is a low frequency oscillator. This drives a higher frequency oscillator 93 which in turn drives an audio alarm 95.

Oscillator 91 may also be driven by a reference supply 97 having an output which is boosted by amplifier 99. The output of amplifier 99 serves as a power supply to all circuits via terminal 101. A low battery circuit 103 serves to check to power level from amplifier 99 and provide a signal to oscillator 91 in the event that there is a low power condition. This condition will also cause the output from oscillator 91 to be transmitted to alarm 95 via high frequency oscillator 93. The reference supply 97 is powered from battery 105, a nickel-cadmium battery which may be recharged through a battery charging circuit 107. This circuit may be connected to certain pins in jack 29a, the same jack which the probe 37 is connected to, except that different pins are used. Similarly, different pins of jack 29 are used to receive an earphone 109 in jack 29b. Thus, a single jack serves to receive the oxygen probe 37, as well as a battery charging circuit 107 and an earphone 109. Use of earphone 109 disables alarm 95 through a switch, not shown.

In operation, the power switch 25 is turned on so that power is applied to all circuits. One of the partial pressure oxygen sensors is then selected by selector 57, depending on whether the probe 37 is plugged into jack 29. Simultaneously, absolute pressure is measured by pressure sensor 73 and the ambient pressure and oxygen partial pressure signals are combined in the summing junction 71. An output signal is then transmitted to display 17 and either the percent oxygen or the ambient pressure may be read in display 17.

Thus, the gauge of the present invention provides a reading of percent oxygen, with automatic compensation for changes in atmospheric pressure.

We claim:

1. An instrument for measuring percent oxygen in air comprising,
   an oxygen partial pressure measurement transducer having automatic temperature compensation, and having a first electrical output,
   an absolute pressure transducer, having automatic temperature compensation, and having a second electrical output,
   a summing junction receiving said first and second electrical outputs and having a transfer function yielding a percent oxygen output signal as a mathematical function of each of said first and second electrical outputs multiplied by a respective constant, and
   a threshold detector for signalling when the percent oxygen output signal is below a preset value.

2. The apparatus of claim 1 wherein said transfer function is additive, combining the sum of the first and second electrical signals.

3. The apparatus of claim 1 wherein a pair of temperature compensated oxygen partial pressure measurement transducers are provided, including a first oxygen transducer within an instrument housing and a second oxygen transducer external to the housing, said pair of transducers connected to a selection switch for choosing the transducer to be employed.

4. The apparatus of claim 3 wherein the second oxygen transducer is mounted in a probe connected to the housing by a cable, a plug and a jack, the jack connected to said selection switch in a manner such that said first oxygen transducer is disabled when said plug is inserted into the jack.

5. The apparatus of claim 1 having a visual readout with a selector switch receiving said percent oxygen output signal and said second electrical output indicative of temperature compensated absolute pressure whereby said visual readout may selectively display percent oxygen and absolute pressure.

6. An instrument for measuring percent oxygen in air comprising, a hand-held housing having an electronic display, a plurality of switches and a multi-pin jack, first and second oxygen partial pressure measurement transducers having automatic temperature compensation, one of said oxygen transducers mounted internally within said housing, the other of said oxygen transducers mounted in a probe external to the housing and connectable to the housing by a cable and a plug, the plug fitting into said jack, said jack connected to a selection switch in a manner such that said oxygen transducer mounted within the housing is disabled when said plug is inserted into the jack, so that a single oxygen transducer produces a first electrical output, an absolute pressure transducer having automatic temperature compensation and mounted within the housing and having a second electrical output, a summing junction receiving said first and second electrical outputs and having a transfer function yielding a percent oxygen output signal as a mathematical function of each of said first and second electrical outputs multiplied by a respective constant, said summing junction mounted within said housing, and an alarm device associated with said housing and connected to a threshold detector within the housing, said alarm device activated when the percent oxygen is below a preset level.

7. The instrument of claim 6 wherein said jack is adapted to receive an earphone.

8. The instrument of claim 6 wherein said jack is adapted to receive a battery charger.

9. The instrument of claim 6 wherein said threshold detector is responsive to a preset value of percent oxygen.

10. The instrument of claim 6 wherein said transfer function is $$\%O_2 = K_1(PO_2) + K_2(760 - P_{amb})$$

where % $O_2$ is the percent oxygen
$K_1$ and $K_2$ are constants
$PO_2$ is the measured oxygen partial pressure
$P_{amb}$ is the measured ambient pressure.

* * * * *